United States Patent [19]

Krupey et al.

[11] Patent Number: 5,658,779

[45] Date of Patent: Aug. 19, 1997

[54] METHOD OF ADSORBING VIRUSES FROM FLUID COMPOSITIONS

[75] Inventors: John Krupey, Glen Rock; Allen D. Smith, Somerset; Edward Arnold, New Brunswick; Robert Donnelly, Highland Park, all of N.J.

[73] Assignee: LigoChem, Inc., Fairfield, N.J.

[21] Appl. No.: 532,118

[22] Filed: Sep. 22, 1995

Related U.S. Application Data

[63] Continuation-in-part of Ser. No. 207,274, Mar. 7, 1994, Pat. No. 5,453,493, which is a continuation-in-part of Ser. No. 854,302, Mar. 20, 1992, Pat. No. 5,294,681.

[51] Int. Cl.$^6$ .................................................. C12N 7/02
[52] U.S. Cl. .................. 435/239; 435/235.1; 525/327.4; 525/327.6; 525/380; 525/382; 525/420; 530/421; 530/418
[58] Field of Search ............................................. 435/239

[56] References Cited

U.S. PATENT DOCUMENTS

| | | | |
|---|---|---|---|
| 3,684,777 | 8/1972 | Field | 575/380 |
| 4,271,028 | 6/1981 | Marfurt | 210/727 |
| 4,421,653 | 12/1983 | Le Dain | 210/692 |

*Primary Examiner*—Fred Zitomer
*Attorney, Agent, or Firm*—Omri M. Behr, Esq.

[57] ABSTRACT

A method of adsorbing from a solution comprising a biological sample viruses which retain their viability and infectivity. The method comprises adjusting the pH of said solution to pH 6.0 to 8.0; adding an effective amount of a water insoluble cross-linked polycarboxylic acid polymer ("WCPP") into said solution in a volume:volume ratio of WCPP to solution of 100:1 to 1:10,000 to form a WCPP-solution mixture; incubating said WCPP-solution mixture for a time sufficient to immobilize said viruses on said WCPP forming a WCPP-virus matrix; and separating said matrix from said solution. This novel method is suitable for removing, purifying, recovering and analyzing viable viruses as well as viral components such as viral proteins and nucleic acids.

22 Claims, 1 Drawing Sheet

FIG. 1  FIG. 2

METHOD OF ADSORBING VIRUSES FROM FLUID COMPOSITIONS

This application is a continuation in part of U.S. patent application Ser. No. 08/207,274, filed Mar. 7, 1994 now U.S. Pat. No. 5,453,493 by Krupey, which a continuation in part of U.S. patent application Ser. No. 07/854,302, filed Mar. 20, 1992, now U.S. Pat. No. 5,294,681.

FIELD OF THE INVENTION

Method for adsorbing viruses that retain their viability and infectivity from aqueous media containing proteins.

BACKGROUND OF THE INVENTION

Conventional methods of purifying viruses and viral nucleic acids have significant faults and shortcomings. Conventional protocols for purifying bacterial and mammalian viruses from host cells or growth media generally contain three steps. First, viruses must be liberated from the host cells. Viruses which lyse the infected cells used to propagate the virus of course are released directly into the growth medium. However, certain other non-enveloped viruses, such as reovirus and adenovirus, are associated with membrane components of the cells and must first be extracted away from this material. A common method of extracting non-enveloped viruses from cellular components is by homogenizing the cell suspension in the presence of Freon 113 as described in Shatkin, A. J., Proc. Natl. Acad. Sci USA 54 1721 (1965). Although effective, care must be taken in performing this procedure, since it produces virus-containing aerosols and releases Freon into the environment.

Second, the virus must be concentrated prior to actual purification. Two methods are commonly used to concentrate and partially purify viruses. Viruses may be precipitated by addition of ammonium sulfate or polyethylene glycol, as discussed in Mahy B. W. J., Ed. *Virology, a practical approach,* Washington D.C. (1985). However, this method usually co-precipitates many other proteins present in the tissue culture medium, and therefore may to some extent reduce the purity of the virus sample. Alternatively, concentration of virus may be achieved by pelleting viruses in a sample via ultracentrifugation, leaving many soluble proteins in the supernatant, followed by the redissolving viruses in a small amount of buffer.

Third, the concentrated virus must be purified from extraneous materials. This last step in the purification process usually is performed by some form of fractionation employing density gradient ultracentrifugation. For example, the purification of reoviruses involves sedimentation banding on sucrose gradients followed by density equilibrium banding on cesium chloride, as described in Smith, R. E. et al., Virology 39 791 (1969), while picornaviruses have traditionally been purified by use of one of the two banding techniques, described in Rueckert, R. R. and M. Pallansch, (1981) Methods in Enzymology 78 315–326).

These conventional methods of isolating viruses from biological fluids, aqueous suspensions or solutions comprising biological fluids, require either exceedingly long times or expensive equipment for the centrifugation; and further require expensive equipment and/or use of toxic chemicals.

One approach to improving virus-isolating techniques has been to selectively adsorb viruses onto a solid material. An ideal adsorbent would selectively adsorb virus under certain conditions from extraneous materials in liquid suspensions, and desorb viable viruses under different condition to permit physical separation of viral particles.

Various synthetic polymeric materials have been employed in this approach. The cross-linked water soluble polymers of U.S. Pat. Nos. 3,224,941 and 3,684,777 are said to absorb water and adsorb, or inactivate, viruses. The water-soluble polymeric materials of U.S. Pat. No. 4,271,028 are said to adsorb viruses across the pH range of 5–10.

Synthetic polymeric materials which are water insoluble have also been employed in attempts to adsorb viruses. Most of these however have been pH insensitive, so that desorption of viruses would not occur upon change of pH. The materials of Johnson et al., Nature 665–667 (1967) were said to be useful for adsorbing viruses from highly dilute aqueous liquids, while the materials of U.S. Pat. No. 4,421,653 were said to adsorb proteins, including viruses.

Certain investigators have employed synthetic water-insoluble polymeric materials to adsorb viruses at acidic pH and to desorb them at elevated pH. However, these materials have generally been used to treat only very high volumes of water intended for drinking. Wallis et al., Applied Microbiology, 1007–1014 (1969); Wallis and Melnick, Water Research, 4 787–796 (1970); Wallis et al., Applied Microbiology, 703–709 (1971); and Wallis et al., Applied Microbiology, 740–744 (1972). Materials used to remove viruses from smaller volumes of aqueous material, such as the polymeric materials disclosed in U.S. Pat. No. 3,398,092, are said to remove or inactivate virus present in water.

LambdaSorb®, from the Promega Corporation (Madison, Wis.) is a further solid material said to be useful in removing virus particles (in particular, bacteriophage lambda particles) from aqueous suspensions. This material is a conjugate of fixed *Staphylococcus aureus* cells and rabbit polyclonal antibodies directed against bacteriophage lambda particles. The adsorbent is shaken with a bacterial cell lysate, then centrifuged at 12,000×g for less than one hour to remove the adsorbent and any bound bacterial virus. An aqueous suspension of the adsorbent is used in a volume ratio of adsorbent to lysate of 1:100. Apparently, the bacteriophage do not desorb from the LambdaSorb, for only disruption of bound bacteriophage particles is disclosed.

Synthetic polymeric materials said to be useful in removing protein from aqueous suspensions are described in U.S. Pat. No. 5,294,681 and U.S. patent application Ser. No. 08/207,274, filed Mar. 7, 1994 by Krupey. These materials are water insoluble polycarboxylic acid compositions. They are added to and mixed with a suspension containing proteins for approximately 15 minutes to allow for formation of a polymer-protein matrix. Depending on the composition's substitution groups, the pH of the suspension is from pH 3 to 7.5. After the matrix is removed from the suspension, it is said the bound proteins may be released therefrom by washing the matrix in buffer solutions at pH 8.6 to 9.5, optionally in the presence of 0.5 to 2% w/w surfactant per volume of matrix pellet.

The techniques for purifying viral nucleic acids generally comprise the conventional virus purification steps enumerated above, followed by disruption of the viral particle with compounds such as surfactants or guanidine thiocyanate, centrifugation to partially purify the nucleic acid material, and electrophoresis. The drawbacks of conventional methods for purifying viruses—long time periods or the use of expensive equipment, and the use of toxic chemical substances—are also encountered in methods for purifying viral nucleic acids.

The nucleic acids purified from mammalian viruses using these conventional methods are fairly pure, since the viruses released into extracellular medium are largely separable from host cells and their components. However, nucleic acids isolated from bacterial viruses using these methods are often not as pure. The electrophoresis gels of conventionally purified bacteriophage nucleic acids typically do not reveal a single sharp band indicative of purity, but instead exhibit an elongated faint smear with several bands, indicating the presence of nucleic acids of many disparate lengths, including molecules longer than the known length of the viral nucleic acid molecule.

A common method for isolating the nucleic acid of bacteriophage lambda is disclosed in *Molecular Cloning, A Laboratory Manual,* 2nd Ed., Sambrook et al., pages 2.73–2.81, Cold Spring Harbor Laboratory Press, (1989). In this method, bacteriophage particles isolated using centifugation techniques are disrupted by exposure to heat, detergent (as a protein denaturant) a chelating agent, such as EDTA. The nucleic acid released by this disruption is isolated and purified from other viral components by phenol/chloroform extraction. Despite the presence of protein denaturants in this method, purified bacteriophage nucleic acid usually contains low levels of bacteriophage exonuclease, which cleaves the viral nucleic acid into many small pieces. An ongoing problem with conventional techniques of bacteriophage nucleic acid isolation is that despite use of heat and chemical denaturants, viral exonucleases and nucleic acid-binding proteins may retain bioactivity, and thus cleave or bind to the released nucleic acid respectively, thus greatly reducing the usefulness of the nucleic acid. Thus, subsequent extraction steps to remove proteins and other extraneous viral material from viral nucleic acid are frequently necessary.

Moreover, where nucleic acid is to be isolated from bacterial viruses adsorbed to a solid material, the use of heat and detergent may denature the protein so much that large amounts of viral protein is desorbed from the solid material by disruption, causing the resulting nucleic acid to contain substantial amounts of viral protein.

LambdaSorb®, described above, is also said to be useful in isolating nucleic acid from bacteriophage. Heat in the presence of EDTA is applied in order to disrupt bacteriophage bound to the solid; the nucleic acid released by the disrupted bacteriophage is then isolated using phenol/chloroform extraction.

SUMMARY OF THE INVENTION

Applicants have now discovered that the cross-linked water insoluble polycarboxylic acid polymers of U.S. Pat. No. 5,294,681 and U.S. patent application Ser. No. 08/207,274, filed Mar. 7, 1994 by Krupey (both incorporated herein by reference) may be employed to adsorb viruses and viral components selectively from a composition comprising a biological fluid. These polymeric materials are able to remove up to 99% of viruses from a sample. When the adsorbed viruses are desorbed at higher pH, they are viable and retain normal levels of infectivity. Thus, adsorption to the polymeric materials do not reduce or destroy the viability of the adsorbed viruses.

There are numerous advantages associated with the novel method. The expensive equipment and toxic chemicals essential to conventional techniques are not necessary in the novel method. Unlike earlier polymeric materials, which were able to adsorb viruses from solutions free of protein, the present invention permits one to bind, isolate and extract viruses and viral components from fluids which do contain proteins. The adsorptivity of the polymeric material employed in the novel method is a function of pH, thus permitting simple, convenient adsorption and desorption of viruses. Desporption of the bound viruses does not harm their viability or infectivity. Alternatively, one may disrupt the bound viruses, so as to purify and/or replicate nucleic acid of bound viruses (as, for example, with the nucleic acid of HIV). The disruption of the bound viruses not only releases viral nucleic acid, but yields whole, uncleaved nucleic acid usually free from viral proteins. Furthermore, the novel method dramatically improves the speed, simplicity and efficiency of virus adsorption and isolation of whole virus or disrupted viral components, i.e., viral protein or nucleic acid. Because the novel method purifies viruses using a series of simple mechanical steps, it is amenable to automation.

There is provided a method for adsorbing viruses from a solution comprising a biological sample containing viruses, the method comprising the steps of a) adjusting the pH of the solution to pH 6.0 to 8.0; b) adding a water insoluble cross-linked polycarboxylic acid polymer ("WCPP") into the solution in a volume:volume ratio of WCPP to solution of 100:1 to 1:10,000 to form a WCPP-solution mixture; and c) incubating said WCPP-solution mixture for a time sufficient to immobilize on said WCPP at least some viruses which are present, forming a WCPP-virus matrix; and d) separating said matrix from said solution.

The WCPP is selected from the group consisting of:

i) a water insoluble cross-linked polyhydroxy polycarboxylic acid obtained by

A) cross-linking a poly(alkylene maleic anhydride) polymer of the formula with an alpha,omega diaminohydroxy alkane of the formula and B) hydrolyzing the unreacted anhydride groups, wherein the molar ratio of the initially charged diaminohydroxy alkane of formula (II) to the initially charged poly(alkylene maleic anhydride) of formula (I) is about 1:1 to 200:1;

ii) a water insoluble cross-linked polycarboxylic acid obtained by cross-linking a poly(alkylene maleic anhydride) polymer of formula (I) with an alpha,omega diamino alkane of the formula $H_2N.(CH)_z.NH_2$, wherein the molar ratio of the initially charged diamino alkane to the initially charged poly(alkylene maleic anhydride) of formula (I) is about 1:1 to 200:1;

iii) a water insoluble cross-linked polyhydroxy polycarboxylic acid having at least two strands, each having a strand skeleton of the formula wherein one carbonyl group of at least one maleoyl moiety thereof in each strand is covalently linked to a —HN.[(H)$_p$(CH)$_z$(OH)$_m$].NH— moiety (IV) to provide the presence between said at least two strands of at least one cross linking unit, said cross linking unit being selected from the group consisting of:

(V)

and (VI)

wherein the ratio of cross linking units to poly(alkylene carbonic acid) strands of formula (III) is between about 1:1 to about 200:1; and iv) a water insoluble cross-linked polycarboxylic acid having at least two strands, each having a strand skeleton of the formula (III)

wherein one carbonyl group of at least one maleoyl moiety thereof in each strand is covalently linked to an alpha,omega diamino alkane of the formula $H_2N.(CH)_z.NH_2$, wherein the molar ratio of the initially charged diamino alkane to the initially charged poly(alkylene maleic anhydride) of formula (III) is about 1:1 to 200:1.

In the group of WCPP, R is phenyl, q is an integer of 7 to 10,000, z is an integer of 1–4, p is 0 or an integer up to z-1, m is 1 or an integer up to z; and y is an integer up to m. Moreover, in the WCPP of this group, the molar ratio of the styrene monomer to the maleic anhydride monomer in the polymer of formula (I) and the strand skeleton of formula (III) is 1:1.

All reagents, macromolecules, enzymes, bacteria, viruses and transgenic organisms disclosed herein are commercially available, or easily producible by persons having ordinary skill in the art by the application of conventional methods.

The WCPP may suitably be selected from the group consisting of the above-described water insoluble cross-linked polycarboxylic acid polymers—i.e., polymers ii) or iv). The volume:volume ratio of the WCPP to the solution may alternatively be from 1:1 to 1:10.

In this method, the pH-sensitive WCPP is able to adsorb viruses when present in a medium having pH 6.0 to 8.0. The pH of the solution comprising the biological sample may therefore be adjusted to pH 6.0 to 8.0 before or after the WCPP is added to this solution.

The viruses of this method are selected from the group consisting of bacterial, plant and animal viruses. Suitable animal viruses include the mammalian enveloped and non-enveloped viruses. The preferred viruses in the novel method are bacterial viruses and non-enveloped mammalian viruses.

The term "solution" as used herein with respect to the novel method (as in the terms "solution comprising a biological sample" and "WCPP-solution mixture") is understood to mean an aqueous, or aqueous-based solution or suspension, comprising water and optionally one or more water-miscible solvents which do not interfere with the ability of the WCPP to adsorb viruses. It is clear from context which "solutions" (such as a "10% formaldehyde solution" or "solution for elution") instead have the standard chemical meaning of that term.

The term "biological sample" is understood to mean herein gaseous, liquid or solid materials from a biological source which can be dissolved, dispersed or suspended, in the "solution." The biological sample may suitably be placed, directly from the biological source, into the "solution" without processing. Alternatively, the biological sample may suitably be pre-processed prior to being added to the solution. For example, blood may be centrifuged to remove leukocytes or solid biological material comminuted to improve solubility or dispersability.

Suitable biological samples which are sources of bacterial viruses include but are not limited to: bacterial cell lysates or clarified liquids, and bacterial growth media supernatants. Suitable biological samples which are sources of plant viruses include but are not limited to: ground plant tissue, plant cell lysate and plant cell culture supernatant. Suitable biological samples which are sources of animal viruses include but are not limited to: exhaled breath; saliva, sputum, vomit, lymph, tears, blood, serum, plasma and other blood derivatives, spinal fluid, synovial joint fluid, semen, menstrual fluid, urine, tissue culture supernatant, tissue culture lysate, organ culture supernatant and organ culture lysate; and tissue, dermal, keratinous, and fecal matter. Gaseous and solid biological samples may be dissolved or suspended in the "solution" by means well known to those skilled in the art. Preferred mammalian biological samples include plasma, whole blood and fractions thereof, and cell culture growth media supernatant.

This method may comprise the further step of adding surfactant to the solution in an amount from 0.01% up to 10%, 0.05 to 1% and 0.01 to 0.4% by volume or weight per volume of said sample, prior to or following the addition of the WCPP to the solution. Suitably, the amount of surfactant is from 0.1 to 1.0% by volume or weight per volume of sample.

There is further provided a method of removing viruses from a solution comprising a biological sample comprising the steps of adsorbing viruses from a solution comprising a biological sample, by the steps described above; and separating the WCPP-virus matrix formed by these steps from the solution to yield a supernatant substantially free of viruses. In this method of removing viruses, the volume:volume ratio of said WCPP to said solution is from 1:1 to 1:10; and the biological sample is selected from the group consisting of serum, plasma, whole blood and fractions thereof, and tissue culture supernatant.

The resulting supernatant which is substantially free of viruses is a useful product, particularly where the initial solution or biological sample is blood or a fraction thereof suspected of containing pathogenic viruses. The removal of such viruses renders such blood or fractions thereof safer for health care workers to handle and discard. Moreover, removal of pathogenic viruses in this manner can afford a therapeutic treatment to patients suffering from viral diseases. Thus, for example, serum from such a patient may be subjected to the method of removing viruses and, after removal of the WCPP-virus matrix, returned to the patient's bloodstream.

There is still further provided a method of concentrating viruses from a solution comprising a biological sample. This method comprises the steps of the method of adsorbing viruses from a solution comprising a biological sample described above, and further comprises the steps of desorbing the immobilized viruses from the WCPP-virus matrix by resuspending the matrix in an eluting buffer of pH 8.0 to 11.0; and collecting the desorbed viruses from the eluting buffer in concentrated form. Where the volume of the eluting buffer is greater than the initial sample volume, the desorbing step may be followed by centrifugation to form a virus pellet. Collection of the pellet thus provides viruses in a smaller, hence in a concentrated form.

There is further provided a method of isolating viral nucleic acid from viruses. Although the steps of this method resemble those of the methods described above, the viruses of this method need not be obtained from a biological sample. This method may be employed to isolate the nucleic acid of viruses regardless of the virus source. The method comprises the steps of a) suspending the viruses in an aqueous solution;

b) adjusting the pH of the solution to from 6.0 to 8.0;

c) adding a WCPP to the solution in a volume:volume ratio of WCPP to solution of 100:1 to 1:10,000 to form a WCPP-solution mixture;

d) incubating the WCPP-solution mixture for a time sufficient to immobilize on the WCPP at least some viruses which are present, forming a WCPP-virus matrix;

e) separating the matrix from said solution;

f) disrupting the viruses immobilized upon the separated matrix to release their nucleic acid; and g) isolating the viral nucleic acid released from the disrupted viruses by means known to those skilled in the art.

In one embodiment of this method, the viruses are those present in a solution comprising a biological sample and the viral nucleic acid obtained is substantially free of host cell nucleic acid.

The nucleic acid isolated by this method may be double or single stranded deoxyribonucleic or ribonucleic acid. This method dramatically improves the speed, simplicity and efficiency of isolating viral nucleic acid, as well as the purity and yield resulting therefrom. This novel method, which uses a solid phase of non-biological origin to bind bacterial virus, simplifies sample manipulation and handling and is therefore less costly than conventional methods. The method provides higher nucleic acid yields with less residual host DNA and RNA than conventional methodologies such as the widely used polyethylene glycol/phenol-chloroform processes. The hazardous solvents used in purifying and disrupting viruses for release of nucleic acid are not used in the novel method. As with the method for adsorbing viruses, this method of isolating viral nucleic acid employs a series of simple mechanical steps, and is therefore amenable to automation.

As noted, the virus in these methods may be a bacterial virus, suitably bacteriophage lambda, T2, T4, T7, P1 or M13. When the virus is a bacterial virus, there is provided a method of adsorbing bacterial viruses from a solution comprising a biological sample. The method comprises the steps of a) cultivating a culture of bacteria known to carry bacterial virus;

b) lysing the bacteria of this culture to form a clarified liquid;

c) adjusting the pH of the clarified liquid to pH 6.0–8.0;

d) adding an effective amount of a WCPP to the clarified liquid in a volume:volume ratio of WCPP to clarified liquid of from 100:1 to 1:10,000 respectively, to form a WCPP-virus matrix; and e) separating the WCPP-virus matrix from said solution.

It is understood that the step of lysing the bacteria may be induced actively by known means (such as sonicating the bacterial cells or chemically inducing their rupture); or may be permitted to occur by allowing the virus to complete its lytic growth cycle.

Further, when the virus is a bacterial virus, there is provided a method of isolating nucleic acid from a bacterial viruses present in a solution comprising a biological sample so that the viral nucleic acid is substantially pure of any bacterial host cell nucleic acid. The method comprises the steps of adsorbing bacterial virus from a solution comprising a biological sample as described above; disrupting said immobilized bacterial viruses; and isolating nucleic acid released from disrupted bacterial virus. The disrupting may suitably be performed by means known to those skilled in the art, e.g., washing the separated WCPP-virus matrix with a chelating agent solution, suitably 1 mM to 100 mM EDTA. The washing of the separated WCPP-virus matrix may suitably be performed at from 25° to 80° C. The nucleic acid may suitably be isolated by means known to those skilled in the art.

When the virus in these methods is a mammalian virus, it is suitably selected from the group comprising adenoviruses; HIV-1; reoviruses; rhinoviruses and genetically engineered variants thereof. Suitably, the virus in these methods is a mammalian virus selected from the group consisting of adenoviruses; HIV-1; reoviruses; rhinoviruses and genetically engineered variants thereof. When the virus is a mammalian virus, there is provided a method of adsorbing mammalian viruses from a solution comprising a biological sample. Despite the acid-sensitivity usually associated with rhinoviruses, these viruses are found, when adsorbed to and later desorbed from the polymer of the novel method, to retain normal levels of infectivity.

In this method, the biological sample is selected from the group consisting of a body fluid of a mammal, or the supernatant of a cell culture. Prior to being exposed to the WCPP, the sample is pretreated to adjust its pH to 6.0 to 8.0. Optionally, surfactant is added. The volume:volume ratio of WCPP to the solution in this method may suitably be 1:1 to 1:10.

More particularly, the biological sample may be selected from the group consisting of blood, serum, blood derivatives, semen, urine, menstrual fluid, spinal fluid, synovial joint fluid, tissue culture supernatant, tissue culture lysate, organ culture supernatant and organ culture lysate. Preferred biological samples include plasma, whole blood and fractions thereof, and cell culture growth media supernatant.

There is further provided a method of concentrating mammalian viruses from a solution comprising a biological sample, wherein the mammalian virus is selected from the group consisting of adenoviruses, HIV-1, reoviruses, rhinoviruses and genetically engineered variants thereof. This method comprises the steps of adsorbing mammalian viruses from the solution, the pH of which is 6.0 to 8.0 according to the method described above; separating the WCPP-virus complex from the solution; and desorbing the immobilized viruses from the matrix by washing the polymer with a buffer solution having pH from 8.0 to 11.0.

When the original biological samples (such as cell culture supernatant, blood or fractions thereof) contain pathogenic viruses, the supernatant products of this method are rendered safer to handle and discard.

There is yet further provided a method of isolating nucleic acid of a mammalian virus such that the isolated nucleic acid is substantially pure of any mammalian host cell nucleic acid. The method comprises the steps of adsorbing mammalian viruses from a solution comprising a biological sample according to the method described above; separating the WCPP to which viruses are immobilized from the solution comprising a biological sample; disrupting the viruses immobilized on the WCPP-virus matrix; and isolating the viral nucleic acid released from the disrupted viruses by means known to those skilled in the art. In this method, as with nucleic acid of bacterial viruses, the step of disrupting may suitably be performed by conventional techniques, as by use of chemical denaturants (including detergents, chaotropic salts and proteinases); chelating agents such as EDTA; or physical conditions such as heat).

The present invention also provides compositions comprising WCPP and a pharmaceutically acceptable excipient. These compositions may be topically applied to adsorb and segregate viruses from the surrounding area. Thus, the composition may be used for virustatic effect in pharmacological, therapeutic or prophylactic products including but not limited to skin cleanser, antiseptic formulations, and contraceptive gels.

There is also provided a method of purifying viral proteins from a solution comprising a biological sample comprising the steps of adsorbing viruses from a solution comprising a biological sample as described above; disrupting the immobilized viruses; incubating the WCPP-solution mixture to permit disrupted viral protein to resorb to said WCPP to form a WCPP-protein matrix; and removing the WCPP-protein matrix from the solution.

A variant of this method is also provided, namely isolating viral proteins substantially free of viral nucleic acids, further comprising the steps of resuspending the WCPP-protein matrix removed from the solution in an alkaline buffer with pH 8.0 to 11.0; and collecting viral protein released from said matrix into said buffer. This pH causes the desorption of said viral protein, and permits collection of viral protein substantially free of nucleic acid.

DETAILED DESCRIPTION OF THE EMBODIMENTS

Definitions

The abbreviations employed herein are defined as follows:

| | |
|---|---|
| EDTA | ethylenediaminetetraacetic acid |
| FBS | fetal bovine serum |
| HEPES | N-2-Hydroxyethylpiperazine-N'-2-ethanesulfonic acid |
| HRV | human rhinovirus |
| MES | 2-[N-Morpholino]ethanesulfonic acid |
| pfu | plaque forming units |
| SM buffer | 50% mM Tris, pH 8.0, 10 mM $MgSO_4$, 0.1% gelatin |
| TCID50 | tissue culture infectious dose (or viral dilution) required to infect 50% of tissue cultures |

The Water Insoluble Polycarboxylic Acid Polymer. The symbols of the atoms shown in the brackets of formula (I) represent the repeating unit of the polymer, and q represents the number of such units in the polymer before cross-linking the polymer with diaminohydroxy alkane. The units as represented by q may vary from 7 to 10,000.

Such a polymer, wherein R is phenyl and q is from 7 to about 250 can be obtained from Scientific Polymer Products, Inc., Ontario, N.Y., U.S.A., under the name styrene-maleic acid anhydride copolymer. A polymer wherein q is from 7 to 10 may also be obtained from Scientific Polymer Products, Inc. and from Atochem Inc., Great Valley Parkway, Malvern, Pa., U.S.A.

In formula (II), z is an integer of 1–4, p is O or an integer up to z-1, and m is 1 or an integer up to z. It is understood each (CH) group in formula (II) has either one or no hydroxyl groups attached thereto. The overall cross-linking moiety has at least one hydroxyl group and may have up to one hydroxyl group per (CH) group in the cross-linking chain, i.e. up to z hydroxyl groups between the two amide groups.

Alpha,omega diaminohydroxy alkanes such as those of formula (II) are commercially available, e.g., 1,3-diamino-2-hydroxy-propane (Aldrich Chemical Co., Milwaukee, Wis.).

Any anhydride groups remaining in the water insoluble cross-linked polyhydroxy polycarboxylic acid are hydrolyzed.

The ratio of the initially charged diaminohydroxy alkane to the initially charged poly(alkylene maleic anhydride) in the WCPP is between about 1 and about 200 to 1 mol/mol.

The WCPP i) is made by cross-linking a polymer of formula (I) with an alpha, omega diaminohydroxy alkane of formula (II), and hydrolyzing the unreacted anhydride groups. A volume of poly(akylene maleic anhydride) conforming to formula (I) is added to a reacting vessel. A volume of alpha, omega diaminohydroxy alkane conforming to formula (II) is also added to the reacting vessel. The ratio of the initially charged diaminohydroxy alkane to the initially charged poly(alkylene maleic anhydride) is between about 1 and about 200 to 1 mol/mol.

The cross-linked polyhydroxy polycarboxylic acid composition is made by cross-linking a polymer of formula (I) with an alpha omega diaminohydroxy alkane of formula (II) and hydrolyzing the unreacted anhydride groups with acid to yield a mixture of compounds of formulae (V) and (VI).

This polymaleic ester (VI) may be readily hydrolyzed back to the parent polyol (V) by mild treatment with a strong base, suitably dilute aqueous alkali at ambient temperature for several hours, preferably at least overnight. Alkaline hydrolysis of the mixture yields substantially pure formula (V).

This is performed typically by mixing the polymer of formula (I) with an alpha, omega diaminohydroxy alkane in water or in an organic solvent such as acetone for 1–5 hours followed by 0–24 hours during which the reaction mixture is allowed to stand at room temperature. The reaction may be carried out at atmospheric pressure at room temperature or elevated temperature. The diaminohydroxy alkane converts by the cross-linking reaction the anhydride groups of the polymer of formula (I) into carboxy and amide groups. Contemporaneously, in amounts depending on the reaction conditions utilized, some of the hydroxyl groups in the linking hydroxydiamido chain are esterified by further reaction with anhydride to form the corresponding "polymaleic ester" (VI). At some time during or after this reaction, unreacted anhydride groups are converted into carboxy groups by hydrolysis in an aqueous medium (as by addition an acid solution to lower pH). While the mixture containing the esterified moieties (VI) is operative for the removal of proteins, it is preferred to hydrolyze these ester moieties by digestions in aqueous alkali, suitably dilute alkali for example 0.05 to 0.5N aqueous sodium hydroxide, suitably at ambient temperature for from about 12 to about 36 hours to yield the pure polyhydroxy compound (V).

After the reaction is completed, an aqueous phase may be added to the mixture, the organic phase removed conventionally, suitably by evaporation under vacuum or by centrifugation with repeated washings with the aqueous phase, and the residue dried at room temperature to provide the WCPP. Finally, the pellet or solid phase is dispersed in water or the desired buffer.

The Biological Fluid and the Virus being Adsorbed. The aqueous medium comprises a biological fluid in diluted or undiluted form containing virus to be removed. The fluid may be selected from a wide range of materials, including bacterial cell lysates, plant extract, and whole human blood.

When the virus being isolated is a bacterial virus, the biological fluid being treated according to the method is derived from a sample of the bacterial virus's host. The fluid may be a liquid culture of the host bacteria, or a supernatant thereof; a suspension of bacteria grown in a solid phase; a cell lysate of the host bacteria; or a liquid suspension of the host bacteria in which a majority of the bacteria have been lysed by the bacterial virus (clarified liquid).

Adsorbing and Desorbing Virus using WCPP. The WCPP may be employed in a method of adsorbing viruses from an aqueous solution comprising a biological sample. This method comprises adding an effective amount of the WCPP to provide a WCPP-virus matrix. It is desirable that the pH of the WCPP containing medium be between about 6.0 to about 8.0 to provide a pH in the WCPP-solution mixture is from about 6.0 to a pH not exceeding about pH 8.0.

It is noted that no one pH is best for adsorbing all viruses. This is in accord with current knowledge of the structure of viruses, the surfaces of which are comprised of proteins and other materials. The optimal pH for adsorption of a particular virus may be therefore determined by methods well known to those skilled in the art without undue experimentation, as for example by evaluating the percentage of virus adsorbed at different pH values.

(Similarly, there is no one pH which is best for desorbing bound viruses from the WCPP-virus matrix. The pH that is best to desorb one virus is often not optimal for a second, particularly where the viral structures differ. Again therefore, the optimal pH for desorption of a particular virus may be determined by methods well known to those skilled in the art without undue experimentation, as for example by evaluating the percentage of virus desorbed at different pH values.)

The WCPP may be added to the aqueous solution containing virus in the form of an aqueous suspension or a dry powder. When the WCPP is suspended in its own aqueous medium prior to being added to the virus-containing aqueous medium, the pH of the WCPP-containing medium is between about 5.5 to about 7.5 to provide a medium after mixture of the components which does not exceed about pH 7.5. Alternatively, where desired, the methods described herein may be performed by passing the solution comprising a biological sample through a bed of WCPP particles or a filter thereof.

The weight ratio of the WCPP to the sample may vary according to the degree of virus removal desired. The optimum ratio is, however, preferably determined in each case having regard to the concentration of virus, the nature and the concentration of the biological sample in the solution being treated, the pH value and the ion concentration.

Typically, the WCPP is incubated with the solution comprising the biological sample for a fixed time, suitably 1 to 60 minutes, of intensive contact, e.g., by stirring or inversion followed by standing. As a result of virus adsorbing to the WCPP, there is formed a WCPP-virus matrix. The matrix may be removed from the solution by any conventional method customary for phase separation (e.g., centrifugation, filtration or sedimentation). The removal of the water insoluble phase provides, thereby, a supernatant from which virus particles have been removed.

After the adsorption of viruses to the polymer occurs, forming a WCPP-virus matrix, it is desirable to centrifuge the reaction mixture to recover the matrix therefrom as a pellet. Where the removal of the water insoluble phase is by centrifugation, the centrifugation should be performed at from about 5 to 100,000×g, preferably 5,000 to 20,000×g for from 0.2 to 10 hours or by settling under unit gravity.

A WCPP prepared by cross-linking styrene maleic anhydride (MW 50,000) with 1,3 diaminohydroxypropane is very effective in binding non-enveloped viruses. The binding efficiency for genetically engineered variants of rhinovirus (such as the HRV14:HIV A:2-1 and HRV14:HIV B:17-1 in Example 4 below, both of which display a portion of the V3 loop of HIV-1 on their surface), reovirus and adenovirus is up to 99 percent from cell culture, supernatants and lysates, and up to about 80% recovery of infectious particles after desorption is achieved.

Viruses may be desorbed from the WCPP-virus matrix by the use of special buffer solutions or other extraction agents such as surfactants. Removal of the virus may be for preparative or analytic purposes. Buffer solutions may be used to separate the virus from the matrix by stirring, grinding and agitating the matrix with a buffer at about pH 8.0 to about 11.0 suitably for from 1 to 60 minutes. There are used about 0.1 to about 10 volumes of buffer, at about pH 8.0 to about 11.0, per volume of pellet of the matrix. The buffer may suitably be Tris buffer which may include surfactant in concentrations ranging from 0.01% to 10% by volume or weight to volume.

Desorbing the virus from the matrix without denaturing said virus may be performed by treating the matrix with a buffer at about pH 8:0 to about 11.0, depending on the virus. Suitably there are used about 0.1 to about 10 volumes of buffer, at about pH 8.0 to about 11.0, per volume of pellet of the matrix. While the invention is not limited thereto, superior results have been obtained where the buffer is a Tris buffer. It is noted that reovirus and genetically engineered variants of rhinovirus such as HRV14:HIV A:2-1 and HRV14:HIV B:17-1, are particularly recoverable from the WCPP-virus matrix.

The step of desorbing virus from the WCPP-virus matrix (as well as of adsorbing virus) may be performed in the presence of a surfactant. Suitable surfactants include but are not limited to Tween-20, Triton X-100, β-octylglucoside, Empigen BB, and CHAPS, sodium lauryl sulfate or N-lauroyl sarcosine. A suitable concentration for the surfactant in the solution is between about 0.01% and about 10%, or 0.05 to 1%, or 0.1 to 0.4% by volume or weight to volume of the WCPP-virus matrix. After the virus is desorbed from or disrupted upon the WCPP, it may be further desirable to rinse the recovered WCPP in a suitable buffer to ready it for further use.

Despite the ability of proteinases, detergents and heat to disrupt bound virus particles, they also denature proteins. Their use to disrupt viruses thus denatures viral coat proteins, and thus facilitates the desorption of viruses, or disrupted virus particles, from the WCPP-virus matrix. This lowers nucleic acid yield, and releases viral proteins in high levels into the viral nucleic acid. Even when proteinases, detergents or heat are used at levels which denature most protein, some protein will remain tightly bound to the viral nucleic acid, by virtue of tight binding. These nucleic acid molecules have limited usefulness, since the bound proteins can block enzyme interactions with the nucleic acid.

Thus, in the novel method, chelating agents are preferably employed substantially free of chemical denaturants to disrupt bound viruses; the resulting nucleic acids are substantially free from viral proteinaceous material. Use of a chelating agent alone disrupts viral particles without interfering with the ability of the WCPP to adsorb viral proteins released by this disruption. Moreover, proteins which bind DNA require $Mg^{2+}$ to do so. The chelating agent not only disrupts the viruses, but by depriving such proteins of magnesium ion, releases them and prevents their re-binding. Thus, use of a chelating agent in the novel method permits one to obtain nucleic acid substantially free of viral proteinaceous material.

Isolation of viral nucleic acid is particularly desirable when working with bacteriophage lambda. Disrupting the phage with detergents or heat typically releases an exonuclease contained by the bacteriophage. Even when heat, proteinase or detergents are present, sufficient levels of bacteriophage exonuclease activity generally remain to cleave the phage nucleic acid into small pieces of reduced usefulness. By contrast, when a chelating agent such as EDTA is used in the novel method to disrupt bound bacteriophage, the resulting nucleic acid is not cleaved by the exonuclease, and has no bound protein. Accordingly, in isolating the nucleic acids of bacterial viruses, it is preferred to perform the disrupting step with a chelating agent substantially free of chemical denaturants or denaturing conditions.

Without in any way restricting the scope of the present invention, Applicants wish to state their understanding of the mechanism by which the WCPP adsorbs virus from an aqueous medium. Precipitability is a function of solubility in an aqueous medium. Solubility in turn is a function at least in part of the degree of a virus particle's hydrophobicity. All virus particles have at least some hydrophobic portions of their surface exposed to the aqueous medium. Applicant believes the WCPP permits the hydrophobic portions of different molecules on the virus surface to approach one another and aggregate to such a degree that the viruses eventually precipitate while the aqueous medium has pH 6.0 to 8.0.

Before this can happen, the WCPP associates with one or more viruses by non-covalent interaction, such as electrical charge attraction. (The WCPP has numerous negative charges which can interact with the partial positive charges present in several points in all protein molecules, e.g. at arginine residues). The local ordering of water imposed by the surface hydrophobic groups is thermodynamically unfavored. Bound water may be released when these hydrophobic groups which are apolar, interact with one another and aggregate. Thus, as two or more viruses interact with the flexible WCPP, like beads on a string, the WCPP string can then enfold such apolar portions of different virus "beads" so that the viruses may aggregate. When the number or size of aggregated viruses is large enough, the WCPP-virus matrix may settle under unit gravity. Applicants further understand that when the pH changes to 8–11, these interactions are reversed, concomitantly releasing virus. The viruses which adsorbed to the WCPP while pH is pH 6.0 to 8.0 desorb in pH 8.0–11.0.

Further, it is believed that disrupting viruses bound to the WCPP in the novel method release far less protein than disrupted viruses bound to conventional polymeric materials. This is believed to be because the WCPP tends to adsorb any free proteinaceous material in ambient pH 6.0 to 8.0. Accordingly, the presence of WCPP in the aqueous medium following viral disruption tends to cause re-adsorption of the majority of viral protein which was released.

In contrast to the WCPP, each antibody of LambdaSorb is highly specific to an individual viral antigen. Polyclonal antibodies contain high numbers of differing antibodies. Thus, each virus is believed to be bound to the solid material by far fewer links than with WCPP. As a result, when bound viruses are disrupted in the LambdaSorb protocol, far higher levels of the disrupted free viral proteins are released into the medium. The ongoing presence of LambdaSorb in the medium results in limited resorption of viral protein; however, most of the disrupted viral protein is believed to remain free, given the low likelihood of each protein encountering an antibody specific to it. Thus, disruption of bacteriophage bound to the LambdaSorb is believed to yield nucleic acids containing far more viral protein than the novel method.

The following Examples are meant to illustrate the present invention and do not restrict the invention in any respect.

EXAMPLE 1

Thirty grams (0.0006 moles) of styrene/maleic anhydride copolymer, MW 50,000, acid number 405, obtained from Scientific Polymer Products, Inc., Ontario, N.Y., is dissolved in 600 milliliters of acetone. To this solution is added a second solution containing 6.6 grams (0.073 moles) of 1,3-diamino-2 hydroxy propane (Aldrich Chemical Company, Milwaukee, Wis.) in 1.8 liters of acetone at a rate of 5.0 mls/min. with constant stirring for a period of 24 hours.

After completion of the reaction, 3 liters of water is added with stirring and then the polymer is allowed to settle under unit gravity. The aqueous organic phase is removed by decantation. The cross-linked polymer is suspended in 1 liter of water and ground for 30 seconds using a Gifford Wood homogenizer (medium setting). The pH of the suspension is adjusted to 1.5 by the addition of hydrochloric acid. After 1 hour the suspension is centrifuged and the aqueous phase is discarded. The pellet is then dispersed in 1 liter of water and the pH of the suspension is adjusted to 10 by the addition of sodium hydroxide and the mixture is stirred for 24 hours. Sodium dodecyl sulfate (SDS) is then added to a final concentration of 1.0% w/v. The suspension is then stirred for 2 hours, centrifuged and the aqueous phase is discarded. The pellet is then resuspended in 1 liter of water, centrifuged and the aqueous phase is discarded. The process of resuspension and centrifugation is repeated at least two more times in order to remove residual SDS.

The pellet containing the polymer is then dispersed in distilled water and converted into its acid (H+) form by the addition of hydrochloric acid to a pH of about 1.5. The suspension is then centrifuged and the supernatant is discarded. The pellet is then repeatedly washed with distilled water and centrifuged until the pH of the wash supernatant reaches 5. The polymer is then washed with 0.01M piperazine-N,N'-bis-2 ethane sulphonic acid (PIPES) buffer pH 6.2 and finally suspended in this buffer to yield a 3.0% w/v suspension.

EXAMPLE 2

Bacteriophage lambda is a versatile cloning vehicle which is valuable in cDNA cloning, genomic DNA cloning and DNA isolation for sequencing and polymerase chain reaction ("PCR"). The purity of bacteriophage lambda DNA isolated by the novel method is compared to that obtained by the conventional PEG/phenol-chloroform extraction.

Two plates (150 mm) of *Escherichia coil* K12 are plated with a recombinant bacteriophage λ gt11 (commercially available from Stratagene Cloning Systems, La Jolla, Calif.) at a density to produce a confluent plate of phage and incubated for 6 hours at 37° C. The plate surfaces are scraped in 10 ml SM (adjusted to pH 6.9) into 50 ml centrifuge tubes. This plate washing is spun in 50 ml conical tubes, 4500 RPM (1000×g), for 10 minutes. The supernatant is removed to new 50 ml centrifuge tubes (approx. 10 ml).

A volume of the WCPP (0.5 of the volume of the supernatant) of Example 1 is added to the centrifuge tube and incubated for 5 minutes at room temperature to form the WCPP-virus matrix, then spun for 5 minutes at 2500 RPM (500×g). The pellet is washed twice with SM (pH 6.9), 50 ml each wash.

The pellet is resuspended with 5.0 ml 10 mM Tris, 1 mM EDTA (TE, adjusted to pH 6.9) and incubated at 65° C. for 10 minutes to disrupt the bacteriophage particles and release their nucleic acid. The nucleic acid is subjected to EtOH precipitate and resuspended in 50 µl TE. The Tris buffer is checked for the presence of DNA by running 10 µl of the buffer on a 1% Agarose gel.

One microgram of the resuspended nucleic acid is treated with the restriction endonucleases Eco RI and Sal I. The enzyme-treated bacteriophage lambda DNA is then run on a 1% agarose gel and photographed.

The protocol for extracting DNA using the PEG/Phenol process is adapted from the Promega "Protocols and Applications Guide", published by Promega, Inc (1994) and incorporated herein by reference. Supernatants containing bacteriophage lambda are obtained as above. Equal volumes of bacteriophage supernatant and precipitation buffer (20% (w/v) PEG 8000, 2M NaCl) are mixed and incubated on ice for 60 minutes. This mixture is spun for 20 minutes at 4500 RPM (1000×g) at 4° C., then resuspended in 1.0 ml phage buffer (20 mM Tris (pH 7.4), 100 mM NaCl, 10 mM MgSO$_4$).

The resuspended pellet is extracted twice with 1 volume TE-saturated phenol/chloroform and extracted once with 1 volume CHCl$_3$: isoamyl alcohol (24:1). The extract is precipitated with an equal volume of isopropanol at –70° C. for 20 minutes. The extract is spun at full speed in microfuge (14,000×g) for 10 minutes and resuspended in TE.

Figure 1:
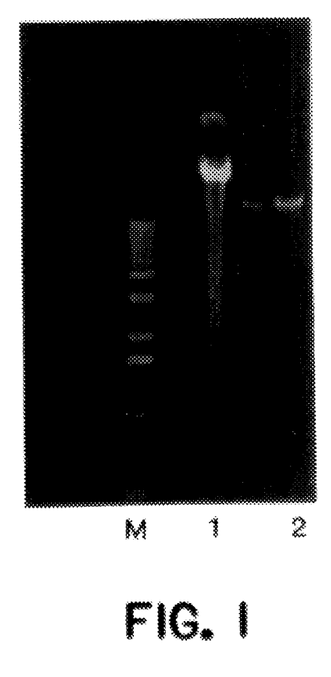
FIG. 1 is a photograph of three lanes of an agarose gel in which DNA has been electrophoresed. Standard compounds of known molecular weight were electrophoresed in lane "M". DNA of bacteriophage lambda isolated by the PEG/phenol-chloroform extraction was electrophoresed in lane 1. DNA of bacteriophage lambda isolated employing the novel method was electrophoresed in lane 2.

The bands of bacteriophage lambda DNA purified by the conventional and novel methods appear in lanes 1 and 2 of FIG. 1 respectively. Lane M illustrates bands of compounds having different known molecular weights. The long streak in Lane 1 indicates the presence of nucleic acid molecules of many differing lengths. Those appearing above the broad bright band are larger polynucleotides than that of bacteriophage lambda; thus the long streak indicates contamination by host cell bacterial DNA. By contrast, lane 2 shows that the DNA isolated using the novel method yields a single sharp band in the agarose gel. This presence of a single band is highly significant, since it demonstrates that the exonuclease activity of the bacteriophage lambda exonuclease, often present in and highly destructive to DNA extracted from the bacteriophage under conventional methods, is not present in the DNA obtained using the novel method. Moreover, the novel method yields this DNA in approximately half the time required to perform the conventional method. Thus, the novel method yields bacteriophage lambda DNA more quickly and with virtually none of the host bacterial nucleic acid impurities of the conventional method.

EXAMPLE 3

Purified bacteriophage lambda DNA may be of limited use if bacteriophage proteins remain in contact with the DNA. Sometimes under conventional methods, proteins remain bound to the phage DNA all through extraction. When they are bound to the DNA, these proteins block other enzymes from cleaving or replicating the phage DNA, and hence greatly reduce the utility of the phage DNA. The bacteriophage lambda DNA isolated using the novel method in Example 2 was therefore examined to determine whether any proteins remained bound thereto.

This determination is made by subjecting the DNA to cleavage by the restriction endonucleases Eco RI and Sal I. Near the center of the bacteriophage lambda DNA, there is a pair of Eco RI cleavage sites and a pair of Sal I cleavage sites adjacent to the Eco RI sites. To determine whether bacteriophage DNA has proteins bound to it, one subjects a first sample of purified bacteriophage lambda DNA to treatment with Eco RI and a second sample to treatment with Sal I. If proteins are bound to the DNA, then one or both samples yield a single bright band on an agarose electrophoresis gel corresponding to the whole, uncleaved bacteriophage DNA. However, if no proteins remain bound to the DNA, both cleavage sites are accessible and treatment with either Eco RI or Sal I yields a characteristic group of cleavage products: In the case of λgt11, the two Eco RI or Sal I sites are set close to one another; cleavage with either restriction endonuclease thus yields two polynucleotides, each approximately 20 kilobases in length.

A sample of the nucleic acid isolated by the novel method from bacteriophage λgt11 in Example 2 is treated with restriction endonuclease Eco RI or Sal I for 60 minutes. Each of these enzyme-treated DNA molecules is then electrophoresed separately on a 1% agarose gel and photographed.

Figure 2:
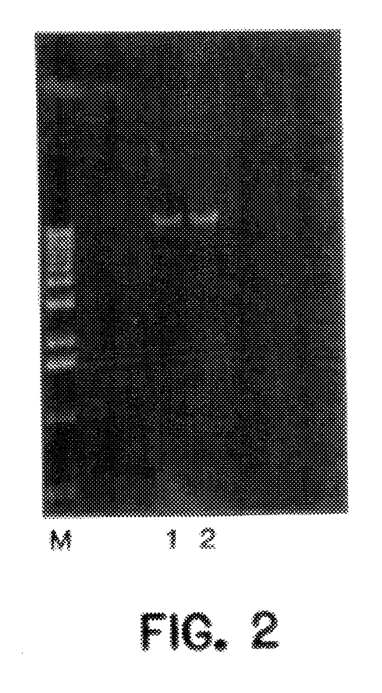
FIG. 2 is a photograph of a further agarose gel in which the DNA purified according to the novel method is digested with either restriction endonuclease Eco RI (Lane 1) or Sal I (Lane 2). Standard compounds of known molecular weight were electrophoresed in lane "M".

As seen in FIG. 2, samples of the bacteriophage lambda DNA purified by the novel method and treated with either Eco RI or Sal I produce a single strong bright band. The right band corresponds to the two polynucleotides which are approximately 20 kilobases in length. Thus, FIG. 2 indicates the bacteriophage lambda DNA purified to the novel method in Example 2 has no bacteriophage protein bound to it and is therefore substantially free of bacteriophage protein.

EXAMPLE 4

The following tests show the ability of four mammalian viruses to bind to and elute from the WCPP of Example 1. The four viruses are 1) a first genetically engineered variant of human rhinovirus which displays a portion of the V3 loop of HIV-1 on its surface (HRV14:HIV A:2-1); 2) a second genetically engineered variant of human rhinovirus which displays a portion of the V3 loop of HIV-1 on its surface (HRV14:HIV B:17-1); 3) reovirus type 3; and 4) adenovirus (strain Ad5d1309). Reovirus type 3 is a commonly used strain. Procedures to obtain adenovirus strain Ad5d1309 are de-scribed in Jones, N. and T. Shenk, Proc. Natl. Acad. Sci. USA 76 3665–3669 (1979). Procedures to obtain HRV14:HIV A:2-1 and HRV14:HIV B:17-1 are described in Smith et al., J. Virology 68 575–579 (1994).

In these tests, the following conditions are used. Virus stocks of chimeric human rhinoviruses, adenovirus Ad5d1309 and reovirus 3 are prepared by propagation in H1-HeLa (obtained from R. R. Rueckert, Institute for Molecular Virology and University of Wisconsin, and Michael G. Rossmann of Purdue University), 293 and mouse L cells, respectively. Prior to use, a supernatant of each of these cell cultures containing virus (typically $1.0 \times 10^6$ to $5.0 \times 10^8$ pfu/ml) is made in 50 mM HEPES pH 6.5, optionally also including 1% by weight of N-lauroyl sarcosine.

Each supernatant is then incubated with the WCPP of Example 1 at a weight ratio of 1 part WCPP to 3 parts supernatant for one hour at room temperature to form a matrix of the virus with WCPP.

The matrix is pelleted by centrifugation for 1 minute at $16,000 \times g$. The amount of infectious virus remaining in the supernatant is quantitated by using a standard plaque forming assay.

Plaque assays are performed using MEM culture medium, prepared as described in Resnick et al., J.Virology, 69 2406–11 (1995), supplemented with fetal bovine serum (5–10%), and antibiotics. HeLa cells are used in the quantitation of human rhinoviruses and adenovirus, while mouse L cells are used for quantitation of reovirus. In these plaque assays, cell monolayers of HeLa or mouse L cells are inoculated with serial dilutions of samples in culture medium containing 2–10% FBS, and incubated for 1 hour at 34.5° C.; overlaid with 0.5%–1.0% agar nobel in culture medium; and incubated 3–7 days at 34.5° C. The cell monolayers are then fixed with a 10% formaldehyde solution and stained with crystal violet.

The pelleted matrix is then washed with a HEPES buffer, pH 6.5, with or without 0.154M NaCl, to remove any free virus as well as other materials not bound in the matrix. The matrix is then resuspended in 100–200 mM Tris, pH 9.0–9.5 with or without added NaCl (0.15M–0.2M) and 1% N-lauroyl sarcosine, depending on which of the conditions defined below is chosen.

A genetically engineered variant of rhinovirus designated A:2-1, purified according to the above protocol, is concentrated by ultracentrifugation. A sample of the concentrated virus is then analyzed by denaturing polyacrylamide gel electrophoresis.

Results: All four non-enveloped viruses are bound by the WCPP of Example 1 (as the data in Table 1 indicates). In addition, conditions in which infectious virus are eluted from the polymer are identified. The purity of human rhinovirus chimera A:2-1 preparations is assessed after concentration by ultracentrifugation, and is judged to be predominantly pure when N-lauroyl sarcosine is included in the binding step.

Other detergents are also assessed for their effect on the purity of human rhinovirus chimera A:2-1 preparation (results not shown). None of Tween-20, Triton X-100, β-octylglucoside, Empigen BB, and CHAPS are as effective as N-lauroyl sarcosine. This result does not mean any or all of these surfactants would be ineffective in the purification of other viruses.

With the exception of Experiment 1 in Tables 2 and 3, each value in the following Tables is the mean of at least two test runs; values marked by an asterisk ("*") are averaged from samples replicated within the same experimental run which are then divided into different groups receiving different solutions for elution. Blank areas in the following Tables indicate a test was not performed. Conditions 1 through 5 are defined following Table 3.

TABLE 1

Binding of genetically engineered variant of HRV virus to WCPP

| | HRV14 A:2-1 | | HRV14 B:17-1 | |
|---|---|---|---|---|
| | % B | % E | % B | % E |
| Condition 1 | 99 | 54 | | |
| Condition 3 | 99 | 55 | 99 | 38 |
| Condition 3 | 96 | 78 | | |
| Condition 3 | 97 | 73 | | |
| Condition 3 | 98 | 80 | | |
| Condition 5 | 99 | 49 | | |

% B - percent bound
% E - percent eluted (based on the amount of virus bound to WCPP)
The results shown for condition 3 are obtained in four separate experiments.

TABLE 2

Binding of Adenovirus to WCPP

| | % B | % E |
|---|---|---|
| Experiment 1 | | |
| Condition 1 | 75 | 0 |
| Condition 3 | 93 | 0 |
| Experiment 2 | | |
| Condition 2 | 96* | 45 |
| Condition 4 | 96* | 55 |
| Experiment 3 | | |
| Condition 2 | 62* | 0 |
| Condition 3 | 36 | 0 |
| Condition 4 | 62* | 0 |

% B - percent bound
% E - percent eluted (based on the amount of virus bound to WCPP)

TABLE 3

Binding of Reovirus to WCPP

| | % B | % E |
|---|---|---|
| Experiment 1 | | |
| Condition 1 | 72 | 14 |
| Condition 3 | 20 | 2 |

TABLE 3-continued

Binding of Reovirus to WCPP

|  | % B | % E |
|---|---|---|
| Experiment 2 | | |
| Condition 2 | 53* | 11 |
| Condition 4 | 53* | 62 |
| Experiment 3 | | |
| Condition 2 | 77* | 0 |
| Condition 3 | 0 | 0 |
| Condition 4 | 77* | 33 |
| Experiment 4 | | |
| Condition 2 | 69* | 5 |
| Condition 3 | 41 | 0 |
| Condition 4 | 69* | 34 |

% B - percent bound
% E - percent eluted (based on the amount of virus bound to WCPP)
Condition 1- binding performed in the absence of detergent; elution buffer used is either 150 mM Tris, pH 9.0 (HRV14:HIV A:2-1) or 200 mM Tris, pH 9.5 (Ad5dl309 and reovirus)
Condition 2- binding performed in the absence of detergent; elution buffer used is 200 mM Tris, pH 9.5, 154 mM NaCl (Ad5dl309) or 200 mM Tris, pH 9.5, 150–200 mM NaCl (reovirus)
Condition 3- binding performed in the presence of 1% N-lauroylsarcosine; elution buffer used is 200 mM Tris, pH 9.5 with (reovirus, Exp. 3 and 4., and adenovirus Ad5dl309, Exp.3) or without (HRV14:HIVA:2-1, HRV14:HIVB:17-1; reovirus, Exp. 1; adenovirus Ad5dl309, Exp 1) 154 mM NaCl
Condition 4- binding performed in the absence of detergent; elution buffer used is 180 mM Tris, pH 9.5, 139 mM NaCl and 1% N-lauroylsarcosine
Condition 5-binding performed in the presence of 1: N-lauroylsarcosine; elution buffer used is 135 mM Tris, pH 9.0, containing 1% N-Lauroyl sarcosine (HRV14:HIV A:2-1)

(It should be understood that while several of the "0" test results in Tables 2 and 3 reflect actual measurements of no virus being present, other data indicate that some virus is present, but at such low levels as to be at the limit of the assay's sensitivity. Rather than calculate the number of viruses present from such possibly unreliable data, these data are considered equivalent to zero.)

EXAMPLE 5

The ability the WCPP to bind HIV-1 is also evaluated using stocks of the HIV-1 IIIB strain (described in Gallo et al., Science 224 500–503 (1984), incorporated herein by reference, and received from Susan Zolla-Pazner, prepared in H9 cells following the procedure of White-Scharf et al., Virology 21: 197–200 (1993), incorporated herein by reference). HIV-1 IIIB stock is diluted into tissue culture medium (RPMI 1640, (Gibco Company, Grand Island, N.Y., catalog number 21870-07) supplemented with 10% FBS, glutamine to 4 mM, and 100 units/ml of penicillin and streptomycin, or human sera, 35 mM MES, pH 6.0 (undiluted, or diluted 1:2 with 25 mM MES, pH 6.5, 0.15M NaCl). The diluted stock is then mixed with the WCPP at a weight ratio of 1:1 or 1:2. After one hour at room temperature, the WCPP is pelleted by centrifugation, and the amount of virus remaining in the supernatant quantitated by 1) a reverse transcriptase assay; and 2) determination of the amount of infectious virus ("TCID50") remaining after treatment with WCPP compared to controls receiving only buffer. TCID50 values are calculated using the method of Reed and Muench, Amer. J. Hygiene 27 493–497 (1938), incorporated herein by reference. Reverse transcriptase activity is measured using the method of Willey, J.Virology 62 139–147 (1988), incorporated herein by reference, and the amount of radioactive label incorporated into product quantitated using a phospho-imager (400E model) from Molecular Dynamics, (Sunnyvale, Calif.).

In order to investigate the ability of the WCPP to bind the enveloped retrovirus HIV-1, a volume of the WCPP of Example 1 is added to RPMI 1640 cell culture medium described above or human serum containing HIV-1. The level of HIV-1 present is determined by measuring the reduction in reverse transcriptase ("RT") activity present in two samples, one having a volume ratio of the WCPP to HIV solution of 1:1, and a second with a ratio of 1:2. The HIV-1 level is also measured by determining the reduction in the infectious titer (TCID50) in two similar samples.

TABLE 4

Binding of HIV-1 to the polyhydroxy polycarboxylic acid composition.

| | RT activity % control | | TCID50 % control | |
|---|---|---|---|---|
| | 1:2[a] | 1:1[a] | 1:2[a] | 1:1[a] |
| Condition 1 | 2 | ND[b] | 4 | ND |
| Condition 2 | 82 | 70 | 50 | 35 |
| Condition 3 | 57 | 16 | 20 | 10 |

[a]volume ratio of WCPP to viral solution
[b]Not Determined
Condition 1- binding from RPMI 1640/10% FBS/50 mM HEPES pH 6.5.
Condition 2- binding from human serum/35 mM MES, pH 6.0
Condition 3- binding from human serum/35 mM MES, pH 6.0 diluted 1:2 with 25 mM MES, pH 6.5, 0.15 M NaCl.

EXAMPLE 6

The following test is performed to determine whether nucleic acid of HIV bound to WCPP is liberated by treatment with a strong protein denaturing solution.

After adsorbing HIV-1 of Example 5 to the WCPP of Example 1, the WCPP-virus matrix is pelleted by centrifugation. The supernatant then is discarded and the pellet washed 3 times with 500 μl of RPMI 1640 without FBS. Five hundred microliters of a 4M guanidine thiocyanate, 0.5% N-lauroyl sarcosine, 20 mM sodium citrate pH 7.0 and 100 mM 2-mercaptoethanol solution is used to resuspend the washed WCPP-virus matrix pellets. After a 5 minute incubation at RT, the matrix is again pelletted by centrifugation.

RNA is extracted from the supernatant using the procedure of Chomczynski and Sacchi (Ann. Biochem. 162:156 (1987), incorporated herein by reference). The viral RNA thus liberated is reverse transcribed into a viral cDNA using Gibco (cat. #28025-D13) M-MLV reverse transcriptase with the buffer supplied by the manufacturer supplemented with dNTPs (0.5 mM), DTT (10 mM), 1 μl of Inhibit-Ace (5'-3') per 20 μl reaction and the following 21 base oligonucleotide primer complementary to the (+) strand viral RNA: (ATTACAGTAGAAAAATTCCCC, SEQ ID NO:1) that starts at base 7381 of the HIV-1 genome. (The numbering scheme used herein for the HIV genome is that of Ratner et al., Nature 313 277–284 (1985), incorporated herein by reference).

A region of the viral cDNA corresponding to the V3 loop of the surface glycoprotein gp120 is then amplified by PCR using the following two primers, a (+) strand 20 base oligonucleotide primer (TACAATGTACACATGGAATT, SEQ ID NO:2) starting at base 6957 and a (−) strand 18 base oligonucleotide primer (CTGGGTCCCCTCCTGAGG, SEQ ID NO:3) ending at 7331. (It is understood that SEQ ID NO:1 and SEQ ID NO:3 are (−) strands, i.e., are complementary to bases in the (+) strand of viral RNA, and thus base pair either to the viral RNA or to later-generated (+) cDNA strands; while SEQ ID NO:2 is a (+) strand complementary to the (−) cDNA strand generated from the RNA and DNA primer SEQ ID NO:1.)

Each PCR reaction contains two units of Vent polymerase (New England Biolabs) in a buffer prepared from a 10X stock supplied by the manufacturer that is supplemented with dNTPs to 0.2 mM and 0.5 μg of each primer. Reactions are hot started by incubation at 94° C. for 2 minutes prior to running the following cycling program; denaturation for 1 minute at 94° C., followed by a 1 minute annealing step at 55° C., and a 1 minute extension step at 72° C. After 35 cycles samples are held at 72° C. for 8 minutes prior to cooling to 4° C.

A sample from each reaction is analyzed on a 2% agarose gel for the expected PCR product of 374 base pairs. A 100 base pair ladder is run as a standard for comparison. Electrophoretic analysis of the products obtained from reverse transcription and PCR of the viral RNA yields a band of the expected molecular weight of 374 base pairs.

We claim:

1. A method of adsorbing viruses from a solution comprising a biological sample containing viruses, said method comprising a) adjusting the pH of said solution to pH 6.0 to 8.0;

b) adding a water insoluble cross-linked polycarboxylic acid polymer ("WCPP") to said solution in a volume:volume ratio of WCPP to solution of 100:1 to 1:10,000 to form a WCPP-solution mixture;

c) incubating said WCPP-solution mixture for a time sufficient to immobilize on said WCPP at least some viruses which are present, forming a WCPP-virus matrix; and d) separating said matrix from said solution;

wherein said WCPP is selected from the group consisting of:

i) a water insoluble cross-linked polyhydroxy polycarboxylic acid obtained by

A) cross-linking a poly(alkylene maleic anhydride) polymer of the formula $$(-CH_2-CH-CH-CH-)_q \quad (I)$$
$$\overset{|}{R} \quad \overset{|}{O=C} \quad \overset{|}{C=O}$$
$$\diagdown O \diagup$$

with an alpha,omega diaminohydroxy alkane of the formula $$H_2N.[(H)_p(CH)_z.(OH)_m].NH_2 \quad (II)$$

B) hydrolyzing the unreacted anhydride groups, wherein the molar ratio of the initially charged diaminohydroxy alkane of formula (II) to the initially charged poly(alkylene maleic anhydride) of formula (I) is about 1:1 to 200:1;

ii) a water insoluble cross-linked polycarboxylic acid obtained by cross-linking a poly(alkylene maleic anhydride) polymer of formula (I) with an alpha,omega diamino alkane of the formula $H_2N.(CH)_z.NH_2$, wherein the molar ratio of the initially charged diamino alkane to the initially charged poly(alkylene maleic anhydride) of formula (I) is about 1:1 to 200:1;

iii) a water insoluble cross-linked polyhydroxy polycarboxylic acid having at least two strands, each having a strand skeleton of the formula $$-CH_2-CH-CH-CH- \quad (III)$$
$$\overset{|}{R} \quad \overset{|}{O=C} \quad \overset{|}{C=O}$$

wherein one carbonyl group of at least one maleoyl moiety thereof in each strand is covalently linked to a $$-HN.[(H)_p(CH)_z.(OH)_m].NH- \text{ moiety} \quad (IV)$$

to provide the presence between said at least two strands of at least one cross linking unit, said cross linking unit being selected from the group consisting of:

$$\begin{array}{c} -CH_2-CH-CH-CH- \\ | \quad | \\ O=C \quad C=O \\ | \quad | \\ HN \quad OH \\ | \\ H_p-[CH]_z-[OH]_m \\ | \\ HN \quad OH \\ | \quad | \\ O=C \quad C=O \\ | \quad | \\ -CH_2-CH-CH-CH- \\ | \\ R \end{array} \quad (V)$$

and $$\begin{array}{cc} R & R \\ | & | \\ -CH_2-CH-CH-CH- & (-CH_2-CH-CH-CH-)_y \\ | \quad | & | \quad | \\ O=C \quad C=O & O=C \quad C=O \\ | \quad | & | \quad | \\ HN \quad OH \text{———} O \quad OH \\ | \\ H_p-[CH]_z-[OH]_{m\pm y} \\ | \\ HN \quad OH \\ | \quad | \\ O=C \quad C=O \\ | \quad | \\ -CH_2-CH-CH-CH- \\ | \\ R \end{array} \quad (VI)$$

wherein the ratio of cross linking units to poly(alkylene carbonic acid) strands of formula (III) is between about 1:1 to about 200:1; and iv) a water insoluble cross-linked polycarboxylic acid having at least two strands, each having a strand skeleton of the formula $$-CH_2-CH-CH-CH- \quad (III)$$
$$\overset{|}{R} \quad \overset{|}{O=C} \quad \overset{|}{C=O}$$

wherein one carbonyl group of at least one maleoyl moiety thereof in each strand is covalently linked to an alpha,omega diamino alkane of the formula $H_2N.(CH)_z.NH_2$, wherein the molar ratio of the initially charged diamino alkane to the initially charged poly(alkylene maleic anhydride) of formula (III) is about 1:1 to 200:1;

where, in said group of WCPP,

R is phenyl, q is an integer of 7 to 10,000, z is an integer of 1–4, p is 0 or an integer up to z-1, m is 1 or an integer up to z;

y is an integer up to m.

2. The method according to claim 1 wherein said WCPP is selected from the group consisting of said water insoluble cross-linked polycarboxylic acid polymers ii) and iv) and said volume:volume ratio of said WCPP to said solution is from 1:1 to 1:10.

3. The method according to claim 1 wherein said viruses are selected from the group consisting of mammalian viruses and bacterial viruses.

4. The method according to claim 3 further comprising adding surfactant to said solution 0.1 to 1.0 by volume or weight per volume of said sample, prior to adding said WCPP to said solution.

5. A method of removing viruses from a solution comprising a biological sample, said method comprising
   a) adsorbing viruses from a solution comprising a biological sample according to claim 1, wherein said volume:volume ratio of said WCPP to said solution is from 1:1 to 1:10 and said biological sample is selected from the group consisting of serum, plasma, whole blood and fractions thereof; and
   b) separating said WCPP-virus matrix from said solution to yield a supernatant substantially free of viruses.

6. A method of concentrating viruses from a solution comprising a biological sample, said method comprising adsorbing viruses from a solution comprising a biological sample according to claim 1, desorbing the immobilized viruses from said matrix by resuspending said matrix in an alkaline buffer with pH 8.0 to 11.0; and collecting the desorbed viruses.

7. A method of isolating viral nucleic acid from viruses, comprising
   a) suspending said viruses in an aqueous solution;
   b) adjusting the pH of said solution to from 6.0 to 8.0;
   c) adding a WCPP to said solution in a volume:volume ratio of WCPP to solution of 100:1 to 1:10,000 to form a WCPP-solution mixture;
   d) incubating said WCPP-solution mixture for a time sufficient to immobilize on said WCPP at least some viruses which are present, forming a WCPP-virus matrix;
   e) separating said matrix from said solution;
   f) disrupting the viruses immobilized upon the separated matrix to release their nucleic acid; and
   g) isolating the viral nucleic acid released from the disrupted viruses.

8. A method of isolating viral nucleic acid from viruses so that said viral nucleic acid is substantially pure of host cell nucleic acid, said method comprising
   a) adsorbing viruses from a solution comprising a biological sample containing viruses according to claim 1, said volume: volume ratio of said WCPP to said solution being from 1:1 to 1:10;
   b) disrupting said viruses immobilized upon said separated matrix to release their nucleic acid; and
   c) isolating the viral nucleic acid released from said disrupted viruses.

9. A method of adsorbing bacterial viruses from a solution comprising a biological sample according to claim 3, comprising
   a) cultivating a culture of bacteria known to carry bacterial virus;
   b) lysing the bacteria of said culture to form a clarified liquid;
   c) adjusting the pH of said clarified liquid to pH 6.0–8.0;
   d) adding an effective amount of a WCPP according to claim 1 to said clarified liquid in a volume:volume ratio of WCPP to clarified liquid of from 100:1 to 1:10,000 respectively, to form a WCPP-virus matrix; and
   e) separating said WCPP-virus matrix from said solution.

10. A method of isolating nucleic acid from bacterial viruses present in a solution comprising a biological sample so that said viral nucleic acid is substantially pure of any bacterial host cell nucleic acid, said method comprising
   a) adsorbing bacterial viruses according to claim 9,
   b) disrupting said immobilized bacterial viruses; and
   c) isolating nucleic acid released from said disrupted bacterial virus.

11. The method according to claim 10 in which said step of disrupting said immobilized virus is performed by suspending said separated matrix in a further aqueous solution comprising 1 mM to 100 mM of EDTA but substantially free of chemical denaturants.

12. The method according to claim 11 wherein said bacterial virus is bacteriophage lambda.

13. A method of adsorbing, according to claim 3, mammalian viruses from a solution comprising a biological sample, wherein said biological sample is selected from the group consisting of a body fluid of a mammal.

14. The method according to claim 13 wherein the volume:volume ratio of said WCPP to said solution is 1:1 to 1:10.

15. The method according to claim 13 wherein said biological sample is selected from the group consisting of plasma, whole blood and fractions thereof, and cell culture supernatant.

16. The method according to claim 13 wherein said mammalian viruses are selected from the group consisting of adenoviruses; HIV-1; reoviruses; and rhinoviruses and genetically engineered variants thereof.

17. A method of concentrating mammalian viruses from a solution comprising a biological sample, wherein said mammalian viruses are selected from the group consisting of adenoviruses; HIV-1; reoviruses; rhinoviruses and genetically engineered variants thereof, said method comprising
   a) adsorbing mammalian viruses from a solution comprising a biological sample according to claim 13;
   b) separating said WCPP-virus complex from said solution; and
   c) desorbing said immobilized viruses from said matrix in a concentrated form.

18. A method of removing mammalian viruses from a solution comprising a biological sample, said method comprising performing the steps of claim 17 upon said solution.

19. A method of isolating nucleic acid of a mammalian virus substantially pure of any mammalian host cell nucleic acid, said method comprising
   a) adsorbing mammalian viruses from a solution comprising a biological sample according to claim 13;
   b) separating said WCPP to which viruses are immobilized from said solution comprising a biological sample;
   c) disrupting said immobilized viruses; and
   d) isolating the viral nucleic acid released from the disrupted viruses.

20. The method according to claim 19 wherein said step of disrupting is performed by washing said WCPP-virus matrix with a buffer solution comprising a denaturing agent.

21. A method of purifying viral proteins from a solution comprising a biological sample, said method comprising
   a) adsorbing viruses from a solution comprising a biological sample containing viruses according to claim 1;
   b) disrupting said immobilized viruses;
   c) incubating said WCPP-solution mixture to permit disrupted viral protein to resorb to said WCPP to form a WCPP-protein matrix; and
   d) removing said WCPP-protein matrix from said solution.

22. A method of isolating viral proteins substantially free of viral nucleic acids, said method comprising
   a) adsorbing viruses from a solution comprising a biological sample containing viruses according to claim 21,
   b) resuspending said WCPP-protein matrix removed from said solution in an alkaline buffer with pH 8.0 to 11.0; and
   c) collecting viral protein released from said matrix into said buffer.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Human immunodeficiency virus type 1

( x i ) SEQUENCE DESCRIPTION: SEQ ID NO:1:

ATTACAGTAG AAAAATTCCC C        21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Human immunodeficiency virus type 1

( x i ) SEQUENCE DESCRIPTION: SEQ ID NO:2:

TACAATGTAC ACATGGAATT        20

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Human immunodeficiency virus type 1

( x i ) SEQUENCE DESCRIPTION: SEQ ID NO:3:

CTGGGTCCCC TCCTGAGG        18